(12) United States Patent
Laroche

(10) Patent No.: US 8,952,206 B2
(45) Date of Patent: Feb. 10, 2015

(54) FORMATE BASED HEAT STABLE SALT MITIGATION IN PHYSICAL SOLVENT ACID GAS ABSORPTION PROCESSES

(75) Inventor: Christophe R. Laroche, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/239,636

(22) PCT Filed: Aug. 24, 2012

(86) PCT No.: PCT/US2012/052177
§ 371 (c)(1),
(2), (4) Date: Feb. 19, 2014

(87) PCT Pub. No.: WO2013/028938
PCT Pub. Date: Feb. 28, 2013

(65) Prior Publication Data
US 2014/0200373 A1    Jul. 17, 2014

Related U.S. Application Data

(60) Provisional application No. 61/527,266, filed on Aug. 25, 2011.

(51) Int. Cl.
C07C 41/34 (2006.01)
B01D 53/14 (2006.01)

(52) U.S. Cl.
CPC ............ C07C 41/34 (2013.01); B01D 53/1425 (2013.01); Y02C 10/06 (2013.01); B01D 2252/20463 (2013.01); B01D 53/1456 (2013.01); B01D 2252/2021 (2013.01); B01D 2252/2025 (2013.01); B01D 2252/2026 (2013.01); B01D 2252/20452 (2013.01); B01D 2252/20468 (2013.01); B01D 2256/245 (2013.01); B01D 2257/302 (2013.01); B01D 2257/304 (2013.01); B01D 2257/306 (2013.01); B01D 2257/308 (2013.01); B01D 2257/406 (2013.01); B01D 2257/408 (2013.01); B01D 2257/504 (2013.01); B01D 2258/02 (2013.01)
USPC .......................................... 568/699

(58) Field of Classification Search
USPC ........................................... 568/699
See application file for complete search history.

(56) References Cited

U.S. PATENT DOCUMENTS 4,808,284 A * 2/1989 Bedell et al. .................. 205/437
5,622,681 A   4/1997 Grierson et al.
5,912,387 A   6/1999 Rooney

* cited by examiner

Primary Examiner — Sikarl Witherspoon

(57) ABSTRACT

There is described a process for reducing the concentration of formate based heat stable salts formed in a physical solvent acid gas absorption process (12) wherein acid gas contaminants such as hydrogen sulfide and carbon dioxide are removed from gas mixtures (30) which include these contaminants. The process comprises the step of contacting the physical solvent containing formate based heat stable salts (46) with a metallic and/or organometallic catalyst (52), preferably the catalyst comprises palladium, zinc, platinum, nickel, or rhodium, and/or salts thereof and/or oxides thereof. The process is particularly suited for physical solvents such as refrigerated methanol, dialkyl ethers of polyethylene glycols, N-methyl-2-pyrrolidones, propylene carbonate, blends of N-acetylmorpholine and N-formylmorpholine, 1,3-dimethyl-3,4,5,6-tetrahydro-2(1H)-pyrimidinone, and the like and particularly gas mixtures containing ammonia as a contaminant.

9 Claims, 1 Drawing Sheet

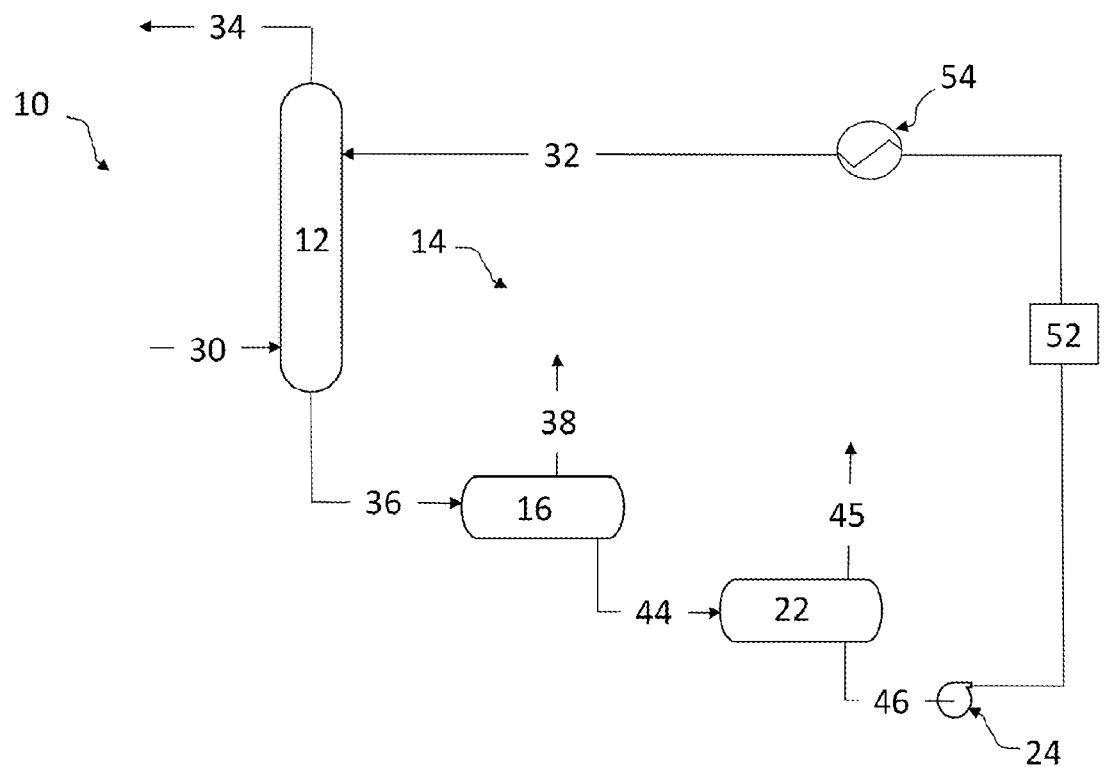

FORMATE BASED HEAT STABLE SALT MITIGATION IN PHYSICAL SOLVENT ACID GAS ABSORPTION PROCESSES

FIELD OF THE INVENTION

The present invention relates to a process for mitigating formate based heat stable salts formed in a physical solvent acid gas absorption process wherein acid gas contaminants such as hydrogen sulfide and carbon dioxide are removed from gas mixtures which include these contaminants. The present invention is particularly suited for physical solvents such as refrigerated methanol, dialkyl ethers of polyethylene glycols, N-methyl-2-pyrrolidones, propylene carbonate, and the like and particularly gas mixtures containing ammonia as a contaminant.

BACKGROUND OF THE INVENTION

Fluid streams derived from natural gas reservoirs, petroleum or coal, often contain a significant amount of acid gases, for example carbon dioxide, hydrogen sulfide, sulfur dioxide, carbon disulfide, carbonyl sulfide, hydrogen cyanide, ammonia, or mercaptans as impurities. Said fluid streams may be gas, liquid, or mixtures thereof, for example gases such as natural gas, refinery gas, hydrocarbon gasses from shale pyrolysis, synthesis gas, and the like or liquids such as liquefied petroleum gas (LPG) and natural gas liquids (NGL). Various compositions and processes for removal of acid gas contaminants are known and described in the literature. For example, it is well-known to treat such fluid streams with chemical solvents, such as amine solutions, which rely on a chemical reaction between the solvent and acid gas contaminants. The amine usually contacts the acidic gas contaminants in the fluid stream as an aqueous solution containing the amine in an absorber tower with the aqueous amine solution contacting the fluid stream counter currently. The regeneration of chemical solvents is achieved by the application of heat.

Alternatively, fluid streams may be treated with physical solvents, such as refrigerated methanol, dialkyl ethers of polyethylene glycols (DEPG), N-methyl-2-pyrrolidones (NMP), propylene carbonate, and the like which do not react chemically with the acid gas impurities. Physical solvents dissolve (absorb) the acid gas contaminants from the fluid stream, typically under high pressure. Since no chemical reactions are involved, physical solvent processes usually require less energy than chemical solvent processes. While the regeneration of chemical solvents is achieved by the application of heat, physical solvents can often be stripped of impurities by reducing the pressure without the application of heat. Physical solvents tend to be favored over chemical solvents when the concentration of acid gases or other impurities is very high. Unlike chemical solvents, physical solvents are non-corrosive, requiring only carbon steel construction.

Acid gas contaminants are removed by contacting the contaminated product gas with fresh solvent in an absorber or other specialized equipment operated under conditions of high pressure and/or low temperature which are favorable for the type of solvent used. Once the contaminants are removed, the decontaminated gas is ready for sale or for additional downstream conditioning, depending on the product stream specifications. The solvent is regenerated for reuse by driving off the absorbed contaminants under low pressure and/or high temperature conditions favorable for desorption. Flash tanks and/or stripper columns are typically used to effect this separation.

The formation of heat stable amine salts (HSAS) has long been a problem in chemical solvents containing amine solutions and formate based heat stable salts (FBHSS) in physical solvents used in gas conditioning. Heat stable salts (HSS) are called heat stable since they are not regenerable in the unit's stripping section. These HSS, such as amine salts of formate, acetate, glycolate, glyoxalate, oxalate, thiocyanate, thiosulfate, sulfate, sulfite and chloride, decrease the acid gas carrying capacity of the solvent and may increase solution viscosity, thus increasing unit operating costs and efficiency.

Several methods are disclosed to neutralize HSAS in amine solutions, for example see U.S. Pat. Nos. 5,622,681 and 5,912,387.

In general, HSAS are less of a problem for physical solvent acid gas removal processes as the solvent is not an amine. However, FBHSS are problematic for physical solvent acid gas removal processes treating a fluid stream containing ammonia as a contaminant. FBHSS may be formed between the ammonia and, for example, formates which are commonly present in low concentrations in physical solvents. If not counter acted, the FBHSS impurity can increase in concentration resulting in impaired efficiency and increased corrosiveness of the solution, which is particularly deleterious for carbon steel construction. Methods used to neutralize HSAS in chemical solvent processes are impractical if not impossible to apply to remove FBHSS a physical solvent process.

As such, it would be advantageous to have process wherein FBHSS are easily, economically, and efficiently removed from physical solvents so as to produce a regenerated physical solvent having an increased useful life and/or a less corrosive nature.

SUMMARY OF THE INVENTION

The present invention is a process for reducing the concentration of formate based heat stable salts in a physical solvent used in an acid gas absorption process comprising contacting the physical solvent containing formate based heat stable salts with a metallic catalyst able to perform the reaction of transformation of formic acid into carbon dioxide and hydrogen, wherein the physical solvent is preferably methanol, one or more dialkyl ether of polyethylene glycols, one or more N-methyl-2-pyrrolidone, propylene carbonate, blends of N-acetylmorpholine and N-formylmorpholine, or 1,3-dimethyl-3,4,5,6-tetrahydro-2(1H)-pyrimidinone.

Preferably, the process disclosed herein above comprises an absorber with a top and a bottom, a high pressure flash tank, a low pressure flash tank, and a heat exchanger wherein the physical solvent contains dissolved contaminants and/or co-absorbed product gas from a fluid stream wherein: i) the solvent emerges from the bottom of the absorber, ii) the solvent passes through a high pressure flash tank where a portion of the dissolved gas contaminants and the co-absorbed product gas desorb from the solvent and emerge from the flash tank as an acid gas stream which may be recycled and returned to the absorber or discharged, iii) the solvent passes through a low pressure flash tank where most of the remaining dissolved contaminants and co-absorbed product gas desorb from the solvent and are released from the flash tank as a discharge gas producing a regenerated solvent, iv) the regenerated solvent is contacted with the metallic catalyst forming a regenerated solvent with reduced formate based stable salts, and v) the regenerated solvent with reduced formate based stable salts passes through the heat exchanger returning to the top of the absorber.

Preferably, in the process disclosed herein above, the metallic catalyst comprises palladium, zinc, platinum, nickel, or rhodium, and/or salts thereof and/or oxides thereof, preferably the metal catalyst is selected from palladium black (Pd/C), Pd(OH)$_2$/C, Pd/AlPO$_4$, Pd/AlPO$_4$—SiO$_2$, Pd/AlPO$_4$—Al$_2$O$_3$, Pd-poly(ethylenimine), Pd/sepiolite, or combinations thereof.

In one embodiment, in the process disclosed herein above the metallic catalyst is an organometallic compound.

In another embodiment, in the process disclosed herein above the metallic catalyst is supported on an inert material.

Preferably in the process disclosed herein above, the metallic catalyst is present in an amount of 2.5 to 250 grams of catalyst to gallon of solvent per minute.

Preferably, in the process disclosed herein above, the temperature of the solvent when contacted by the metallic catalyst is from 0° C. to 200° C.

BRIEF DESCRIPTION OF THE DRAWINGS

FIG. 1 is schematic illustration of a generic physical solvent acid gas removal process.

DETAILED DESCRIPTION OF THE INVENTION

A physical solvent acid gas removal process is based on the solubility of the acid gases, for example carbon dioxide (CO$_2$), hydrogen sulfide (H$_2$S), sulfur dioxide (SO$_2$), carbon disulfide (CS$_2$), carbonyl sulfide (COS), hydrogen cyanide (HCN), ammonia (NH$_3$), mercaptans and the like, within the solvent, instead of on chemical reactions between the acid gas and the solvent. Solubility depends primarily on partial pressure and secondarily on temperature. Higher acid-gas partial pressures and lower temperatures increase the solubility of H$_2$S, CO$_2$, etc. in the solvent and thus decrease the acid-gas components. Various organic solvents are used to absorb the acid gases. Regeneration of the solvent is accomplished by flashing to lower pressures and/or stripping with solvent vapor or inert gas. Some solvents can be regenerated by flashing only and require no heat. Other solvents require stripping and some heat, but typically the heat requirements are small compared to chemical solvents.

The simplest version of a physical solvent process involves absorption followed by regeneration of the solvent by flashing to atmospheric pressure or vacuum, or by inert gas stripping. If H$_2$S is present at only very low concentrations or is entirely absent, this flow scheme is usually applicable since CO$_2$ concentrations as high as 2 or 3 percent can often be tolerated in the product gas. When H$_2$S is present in significant amounts, thermal regeneration is usually necessary to accomplish the thorough stripping of the solvent needed to reach stringent H$_2$S purity requirements. Some physical solvents, such as propylene carbonate, cannot be thermally regenerated since they are unstable at the high temperature required to completely strip H$_2$S from the rich solvent. Heat requirements are usually much less for physical solvents than for chemical solvents such as amines since the heat of desorption of the acid gas for the physical solvent is only a fraction of that for chemical solvents. The circulation rate of the physical solvent may also be less, particularly when the acid gas partial pressure is high.

A physical solvent process for removing gas contaminants from a fluid stream is shown in FIG. 1. It should be understood that the process depicted in FIG. 1 is representative, but not inclusive, of physical solvent processes, one skilled in the art knows there are many variations tailored for specific fluid streams, physical solvents, acid gas impurities, etc. Common features for physical solvent acid gas absorption processes include the fluid stream contacting the physical solvent using counter-current flow in the absorber. Rich solvent from the absorber bottom is flashed in stages to a pressure near atmospheric. This causes the acid-gas partial pressure to decrease; the acid gases evolve to the vapor phase and are removed. The regenerated solvent is then pumped back to the absorber.

As shown in FIG. 1, the system, generally designated 10, comprises an absorber 12 and a recycle loop, generally designated 14 which includes a high pressure flash tank 16, a low pressure flash tank 22, a circulation pump 24, and a distillation unit 26. A fluid stream such as a product gas containing gas contaminants, for example natural gas contaminated with hydrogen sulfide and carbon dioxide, enters the bottom of the absorber 12 through line 30 and is brought into intimate contact with a regenerated physical solvent which enters near the top of the absorber through line 32. The absorber is a conventional absorber tower of a type well-known to those skilled in the art, and the regenerated physical solvent contacts the product gas in the absorber.

A specified amount of the gas contaminants contained in the product gas are removed by the solvent in the absorber 12, and decontaminated product gas, i.e., product gas having the specified amount of contaminants removed, is discharged from the top of the absorber through line 34. Typically, substantially all of the gas contaminants are removed from the product gas in the absorber 12; however, as is well-known to those skilled in the art, this is not always the case, and the amount of contaminants removed depends on the particular use to which the decontaminated product gas stream will be put.

Rich solvent, which now contains dissolved contaminants and/or co-absorbed product gas, emerges from the bottom of the absorber 12 and passes through line 36 to the recycle loop 14 where the solvent is partially regenerated. The rich solvent passes to the high pressure flash tank 16, where a portion of the dissolved gas contaminants and the co-absorbed product gas desorb from the solvent and emerge from the flash tank 16 as an acid gas stream which may be recycled and returned to the absorber 12 or discharged. As noted above, the loop 14 is designated as a "high pressure recycle loop" because the flash tank 16 operates at a pressure below the operating pressure of the absorber but above the regeneration pressure in the flash tank 22.

The physical solvent, now containing only a residual portion of dissolved gas contaminants and co-absorbed product gas, emerges from the high pressure flash tank and passes through line 44 to the low pressure flash tank 22. Most of the remaining dissolved contaminants and co-absorbed product gas desorb from the solvent in flash tank 22 and are released from the flash tank through line 45 as a discharge gas. The fully regenerated solvent emerges from the low pressure flash tank 22 and moves through line 46 to recycle pump 24. The recycle pump delivers the regenerated solvent to line 32 and back to the absorber 12. It should be understood that the regeneration of the solvent is not limited to the use of the illustrated low pressure flash tank. Solvent regeneration can occur in one or more stages using a plurality of flash tanks and/or stripper units and/or distillation units or other suitable equipment, in a manner which is well-known in the art.

Those skilled in the art will recognize that it is necessary to maintain thermal balance within the system shown in FIG. 1. For example, a heat exchanger 54 may be required between the pump 24 to adjust the temperature of the solvent prior to returning the solvent to the absorber 12 through line 32. Temperature requirements differ for different physical solvents and can be determined easily by one skilled in the art.

For example, for dimethyl ether of polyethylene glycol the solvent entering the absorber is at a temperature of from about 10° F. to about 120° F., and preferably from about 10° F. to about 40° F. Accordingly, heat exchange capacity can be added as required to insure that the solvent is at an appropriate temperature prior to being returned to the absorber and/or to otherwise maintain thermal balance within the system.

The process of the present invention to remove formate based heat stable salts (FBHSS) from physical solvents may be used with any suitable physical solvent used in a physical solvent acid gas treating process. While the following list of physical solvents is not comprehensive, preferred physical solvents for use in the present invention are dimethyl ether of polyethylene glycol (DEPG), propylene carbonate (PC), N-methyl-2-pyrrolidone (NMP), methanol (MeOH), blends of N-acetylmorpholine and N-formylmorpholine, and 1,3-dimethyl-3,4,5,6-tetrahydro-2(1H)-pyrimidinone (DMTP). For a good comparison of physical solvents see B. Burr and L. Lyddon, "*A comparison of physical solvents for acid gas removal*", Tech. Rep, Bryan Research & Engineering, Bryan, Tex., USA (2008)

DEPG is a mixture of dimethyl ethers of polyethylene glycol ($CH_3O(C_2H_4O)_nCH_3$ (n is from 2 to 9) used in what is referred to as the SELEXOL process to physically absorb $H_2S$, $CO_2$, and mercaptans from gas streams, for example see U.S. Pat. No. 6,203,599 which is incorporated herein in its entirety. Solvents containing DEPG are licensed and/or manufactured by several companies including Coastal Chemical Company (as COASTAL™ AGR), Dow (SELEXOL™), and UOP (SELEXOL). Other process suppliers such as Clariant GmbH of Germany offer similar solvents. Clariant solvents are a family of dialkyl ethers of polyethylene glycol under the GENOSORB™. DEPG can be used for selective $H_2S$ removal which requires stripping, vacuum stripping, or a reboiler. The process can be configured to yield both a rich $H_2S$ feed to the Claus unit as well as bulk $CO_2$ removal. Selective $H_2S$ removal with deep $CO_2$ removal usually requires a two-stage process with two absorption and regeneration columns. $H_2S$ is selectively removed in the first column by a lean solvent that has been thoroughly stripped with steam, while $CO_2$ is removed in the second absorber. The second stage solvent can be regenerated with air or nitrogen for deep $CO_2$ removal, or using a series of flashes if bulk $CO_2$ removal is required. DEPG also dehydrates the gas and removes HCN. DEPG requires no water wash to recover solvent due to very low vapor pressure. DEPG is suitable for operation at temperatures up to 347° F. (175° C.). The minimum operating temperature is usually 0° F. (−18° C.).

There are a number of methanol processes for acid gas removal including the RECTISOL™ process (licensed by Lurgi AG) and IFPEXOL™ (Prosernat). The RECTISOL process operates at a very low temperature and is complex compared to other physical solvent processes. The main application for the RECTISOL process is purification of synthesis gases derived from the gasification of heavy oil and coal rather than natural gas treating applications. The two-stage IFPEXOL process can be used for natural gas applications. IFPEX-1 removes condensable hydrocarbons and water, and IFPEX-2 removes acid gas. Processing conditions and equipment are very different from the other solvents. Methanol has a relatively high vapor pressure at normal process conditions, so deep refrigeration or special recovery methods are required to prevent high solvent losses. Water washing of effluent streams is often used to recover the methanol. The RECTISOL process preferably operates below 32° F. (0° C.) and may be operated at temperatures as low as −95° F. (−70.5° C.). The process usually operates between −40° F. and −80° F. (−40° C. and −62° C.). Due to low temperatures, approximately 5% of the material in a RECTISOL plant is stainless steel.

The PURISOL™ process which uses NMP is licensed by Lurgi AG. The flow schemes used for this solvent are similar to those used for DEPG. The process can be operated either at ambient temperature or with refrigeration down to about 5° F. (−15° C.). NMP has a relatively high vapor pressure compared to DEPG or PC, and water washing of both the treated gas and the rejected acid gases for solvent recovery is recommended. NMP cannot be used for simultaneous gas dehydration if a water wash is used. In general, NMP recovery with water is not necessary if the PURISOL process is operated at sub ambient temperatures. NMP has the highest selectivity of all the physical solvents considered here for $H_2S$ over $CO_2$. COS is not as soluble as $H_2S$. The Purisol process is particularly well suited to the purification of high-pressure, high $CO_2$ synthesis gas for gas turbine integrated gasification combined cycle (IGCC) systems because of the high selectivity for $H_2S$. Extreme purity with regard to sulfur compounds is not normally required for such fuel gas, and carbon dioxide in the purified gas expands through the gas turbine to provide additional power.

The FLUOR™ SOLVENT process which uses PC is licensed by Fluor Daniel, Inc. PC is available as JEFFSOL™ PC solvent and is particularly advantageous in treating syngas. PC has an advantage over the other solvents when little or no $H_2S$ is present and $CO_2$ removal is important. PC has lower solubilities of the gas being purified: light hydrocarbons in natural gas and hydrogen in synthesis gas. This lower solubility results in lower recycle gas compression requirements for the gas flashed from the rich solvent at intermediate pressures, and lower hydrocarbon losses in the $CO_2$ vent gas stream. An intermediate pressure absorber to remove $CO_2$ greatly reduces the volume of gas to be recompressed. Feed chilling reduces absorption of hydrocarbons, for example chilling the feed to 0° F. (−18° C.) condenses most of the hydrocarbons. PC requires no water wash to recover the solvent due to its low vapor pressure. The operating temperature for PC is limited to greater than 0° F. (−18° C.) and a maximum operating temperature of 149° F. (65° C.).

U.S. Pat. No. 6,102,987, which is incorporated herein by reference in its entirety, discloses a process for removal of $CO_2$ and sulfur compounds from natural gas and raw synthesis gas with a mixture of N-formylmorpholine and N-acetylmorpholine (available as MORPHISORB™ from Uhde) at temperatures between −20° C. and +40° C. at pressure of 10 to 150 bar in absorbing operation.

U.S. Pat. No. 5,413,627, which is encorporated herin by reference in its entirety, discloses the selective removal of $H_2S$ and COS from $CO_2$ using a physical scrubbing agent comprising a heterocycle having five or more ring atoms, which contains two heteroatoms, one of which is nitrogen and the other of which is oxygen or nitrogen. The nitrogen atom present in the ring is/are either double bonded or single bonded but, if single bonded, the nitrogen is organo-substituted. A wide variety of scrubbing agents are disclosed, including 1,3-dimethyl-3,4,5,6-tetrahydro-2(1H)-pyrimidinone (DMTP).

Formic acid ($H_2CO_2$) is present in gas streams comprising carbon monoxide (CO) because of the equilibrium existing between CO, $CO_2$, and $H_2CO_2$:

$$HCOOH \leftrightharpoons CO + H_2O$$

$$HCOOH \leftrightharpoons CO_2 + H_2$$

$$CO + H_2O \leftrightharpoons HCOOH \leftrightharpoons CO_2 + H_2$$

Formic acid may easily be stripped from a physical solvent during regeneration. However, when bases such as ammonia are present, formate based heat stable salts (FBHSS) are formed which cannot be stripped due to their ionic nature. Unless the FBHSS is removed, or otherwise mitigated, it builds up over time. It is well known that the corrosion rate in acid gas removal equipment increases as the level of HSAS, in particular FBHSS, increase, see "Effect of Heat Stabile Salts on MDEA Solution Corrosivity Parts 1 & 2", P. C. Rooney, T. T. Bacon, and M. S. DuPart, GAS/SPEC Technology Group, HYDROCARBON PROCESSING, March 1996, pages 95-103 and April 1997 issue, pages 65-71.

S. Rajagopal, A. R Spatola in *Applied Catalyst A: General* 152 (1997) 69-81 describes the use of palladium black to achieve an efficient transformation of formate anions into $CO_2$ and $H_2$. The concept is well known in the art to achieve hydrogenation reaction where hydrogen gas was not a desirable starting material. We have found that the concentration of FBHSS maybe effectively reduced by applying this strategy to a physical solvent comprising FBHSS. Preferably, the physical solvent comprising FBHSS is contacted with a metallic catalyst able to perform the reaction of transformation of formic acid into carbon dioxide and hydrogen. Any suitable metallic catalyst comprising, but not limited to, palladium, zinc, platinum, nickel and rhodium metals, salts or oxides can be employed in the process of the present invention, for example palladium black, Pd/C, Pd(OH)$_2$/C, Pd/AlPO$_4$, zinc powder, Raney nickel, and the like. In one embodiment, the metallic catalyst is an organo metallic compound, such as Pd-poly(ethylenimine), Wilkinson's catalyst (ClRh(PPh$_3$)$_3$), or Crabtree's catalyst ((Pyr)Ir(1,5-cyclo-octadiene)(PCy$_3$)). In a preferred embodiment, the metallic catalyst or the organometallic compound can be supported on an inert material, for example Pd/AlPO$_4$—SiO$_2$, Pd/AlPO$_4$—Al$_2$O$_3$, Pd/sepiolite, and the like.

The physical solvent comprising FBHSS may be contacted by the metallic catalyst at any time during the regeneration process once the acid gas rich solvent has left the bottom of the absorber column 12 and before the regenerated solvent reenters the top of the absorber column 12. In a preferred embodiment, the physical solvent comprising FBHSS is contacted with the metallic catalyst prior to temperature reduction through the heat exchanger 54. Preferably contact between the metallic catalyst and the physical solvent comprising FBHSS occurs while the solvent is warm having a temperature of from 0° C. to 200° C., preferably 0° C. to 100° C. In a preferred embodiment, the physical solvent comprising FBHSS is contacted 52 by the organometallic compound, for example in a surge tank, after leaving the low pressure flash tank 22 and before entering the heat exchanger 54.

The metallic catalyst is present in an amount of equal to or greater than 2.5 gram of catalyst to gallon of solvent per minute (g/gal/min), preferably 5 g/gal/min, more preferably 10 g/gal/min. The metallic catalyst is present in an amount of equal to or less than 250 gram of catalyst to gallon of solvent per minute, preferably 100 g/gal/min, more preferably 50 g/gal/min.

EXAMPLES

In Examples 1 and 2 and Comparative Example A, a solution containing 277.5 grams (g) dimethyl ether of polyethylene glycol (available from The Dow Chemical Company under the tradename SELEXOL Solvent), 22.5 g water, and 0.5 to 1 g ammonia is placed in a round bottom flask. In addition to dimethyl ether of polyethylene glycol, water, and ammonia, Example 1 further contains 0.5 g of zinc powder available as 94 percent pure available from Fisher Scientific. In addition to dimethyl ether of polyethylene glycol, water, and ammonia, Example 2 further contains 0.06 g of palladium on activated carbon available from Fisher Scientific. The solutions are stirred and refluxed until about 15 g of water is collected via distillation. The solution is replenished with about 15 g of water and the reflux/15 g sample collected/replaced is repeated 5 times. A sample of the solution remaining in the round bottom flack is taken each time between the removal of the 15 g aliquots, the samples are analyzed for their formate anion content by ion chromatography and results reported in grams in Table 1.

Ion chromatography is performed using IONPAC™ AS5A-5 micrometer analytical column with solvent generator on a dionex LC25 instrument.

TABLE 1

| Aliquot | Comparative Example A [formate], g | Example 1 [formate], g | Example 2 [formate], g |
|---|---|---|---|
| 1 | 0.921 | 0.613 | 1.042 |
| 2 | 0.918 | 0.519 | 0.946 |
| 3 | 0.883 | 0.392 | 0.471 |
| 4 | 0.825 | 0.289 | 0.335 |
| 5 | 0.803 | 0.210 | 0.221 |
| 6 | 0.752 | 0.120 | 0.146 |

Without a metallic catalyst, the amount of FBHSS removed from the dimethyl ether of polyethylene glycol solution is 18 percent (Comparative Example A), When a metallic catalyst is used, the amount of F BHSS removed increases to 80 percent and 86 percent for Example 1 and Example 2, respectively.

The invention claimed is:

1. A process for reducing the concentration of formate based heat stable salts in a physical solvent used in an acid gas absorption process comprising contacting the physical solvent containing formate based heat stable salts with a metallic catalyst able to perform the reaction of transformation of formic acid into carbon dioxide and hydrogen.

2. The process of claim 1 wherein the metallic catalyst comprises palladium, zinc, platinum, nickel, or rhodium, and/or salts thereof and/or oxides thereof.

3. The process of claim 1 wherein the metallic catalyst is an organometallic compound.

4. The process of claim 1 wherein the metallic catalyst is supported on an inert material.

5. The process of claim 1 where in the metallic catalyst is selected from palladium black, Pd/C, Pd(OH)$_2$/C, Pd/AlPO$_4$, Pd/AlPO$_4$—SiO$_2$, Pd/AlPO$_4$—Al$_2$O$_3$, Pd-poly(ethylenimine), Pd/sepiolite, or combinations thereof.

6. The process of claim 1 wherein the metallic catalyst is present in an amount of 2.5 to 250 grams of catalyst to gallon of solvent per minute.

7. The process of claim 1 wherein the temperature of the solvent when contacted by the metallic catalyst is from 0° C. to 200° C.

8. The process of claim 1 wherein the physical solvent is methanol, one or more dialkyl ether of polyethylene glycols, one or more N-methyl-2-pyrrolidone, propylene carbonate, blends of N-acetylmorpholine and N-formylmorpholine, or 1,3-dimethyl-3,4,5,6-tetrahydro-2(1H)-pyrimidinone (DMTP).

9. The process of claim 1 comprising an absorber with a top and a bottom, a high pressure flash tank, a low pressure flash tank, and a heat exchanger wherein the physical solvent contains dissolved contaminants and/or co-absorbed product gas from a fluid stream wherein:
- i. the solvent emerges from the bottom of the absorber,
- ii. the solvent passes through a high pressure flash tank where a portion of the dissolved gas contaminants and the co-absorbed product gas desorb from the solvent and emerge from the flash tank as an acid gas stream which may be recycled and returned to the absorber or discharged,
- iii. the solvent passes through a low pressure flash tank where most of the remaining dissolved contaminants and co-absorbed product gas desorb from the solvent and are released from the flash tank as a discharge gas producing a regenerated solvent,
- iv. the regenerated solvent is contacted with the metallic catalyst forming a regenerated solvent with reduced formate based stable salts, and
- v. the regenerated solvent with reduced formate based stable salts passes through the heat exchanger returning to the top of the absorber.

\* \* \* \* \*